(12) United States Patent
Laudenslager et al.

(10) Patent No.: US 6,168,109 B1
(45) Date of Patent: Jan. 2, 2001

(54) APPLICATOR FOR A WRAP FOR A BOXER'S HAND

(75) Inventors: Andrew R. Laudenslager; Peter B. Pecsvaradi, both of Allentown, PA (US)

(73) Assignee: Balazs Inc., Allentown, PA (US)

(*) Notice: Under 35 U.S.C. 154(b), the term of this patent shall be extended for 0 days.

(21) Appl. No.: 09/228,142

(22) Filed: Jan. 11, 1999

(51) Int. Cl.⁷ .......................... B65H 23/06; B65H 75/18; B65H 75/14; B65D 85/02
(52) U.S. Cl. .................................... 242/422.4; 242/422.9; 242/407; 242/588.2; 242/610; 242/118.4; 242/118.7; 242/905
(58) Field of Search ............................ 242/405.3, 422.4, 242/422.9, 588.2, 610, 610.4, 118.7, 407, 118.4, 905; 206/805

(56) References Cited

U.S. PATENT DOCUMENTS

| | | | |
|---|---|---|---|
| 1,121,905 | 12/1914 | Dorricott | 242/613.1 |
| 1,563,036 | 11/1925 | MacAleese | 242/588 X |
| 2,124,063 | * 7/1938 | Harris, Jr. | 206/805 |
| 3,738,589 | * 6/1973 | Brayman | 242/422.4 |
| 4,179,081 | * 12/1979 | Parry | 242/422.4 |

FOREIGN PATENT DOCUMENTS 749211   7/1933   (FR).

* cited by examiner

Primary Examiner—John Q. Nguyen
(74) Attorney, Agent, or Firm—Richard P. Gilly

(57) ABSTRACT

An applicator stores a boxer's hand wrap substantially without folds, creases, or wrinkles, all of which are especially severe if the hand wrap is relatively stiff with dried perspiration. By storing the hand wrap in a smooth, rolled configuration, it can be readily reapplied in a similarly smooth, non-wrinkled manner, as is optimal for boxing purposes. The applicator has a spool and outwardly extending spindles. The spool is non-rotatable relative to the spindle, permitting the wrap to be appropriately tensioned while it is being applied to the boxer's hand. The applicator has deodorant which permeates the wrap when it is stored on a receiving surface of the spool.

22 Claims, 5 Drawing Sheets

APPLICATOR FOR A WRAP FOR A BOXER'S HAND

FIELD OF THE INVENTION

This invention relates to articles of manufacture and, in particular, to an applicator for facilitating the correct placement of cloth wraps on a boxer's hand.

BACKGROUND OF THE INVENTION

Boxers generally enwrap their hands with a length of web-like cloth or tape material prior to inserting their hands in their respective gloves. Such hand wraps are very important to protect the boxers' hands from injury during their practice of the sport. Other sports participants who either offensively or defensively receive blows or forces against their hands, such as football players, may also use similar hand wraps.

The web used to wrap a hand generally must be applied while under a certain amount of tension to assure that it will remain in place during the contemplated activities. Similarly, in order to avoid discomfort or uneven protection, the flexible, generally planar material must be applied with a minimal amount of creases, wrinkles or twists.

The need for the proper amount of tension and the need for a wrinkle-free, crease-free application of the wrap generally mean that two hands are needed to hold, control, and apply the wrap to the boxer's hand in question. Obviously, since one of the boxer's hands is being wrapped, the boxer him- or herself cannot supply the two hands required.

This generally means that a second person, such as a trainer or instructor, needs to assist the boxer in applying the hand wraps. In this manner, a suitable amount of tension is imparted to the wrap and a suitably crease-free and wrinkle-free application is accomplished.

While using a second person to apply hand wraps may not be onerous for boxers who have their own personal trainers on hand to assist them, a great many of boxers and other sports enthusiasts do not have the luxury of a trainer or even the availability of a second person to assist in applying hand wraps. Such boxers must go to the trouble of seeking out and "borrowing" a pair of hands from another boxer of bystander. If none such individual is available, the boxer often must make do with substandard hand wraps and the less-than-optimal protection they afford. This situation is obviously undesirable.

Removing, storing and reapplying the length of cloth or tape material used for boxers' hand wraps also suffers from various inconveniences and drawbacks under current practice. In particular, there is no structure available for effectively removing and storing hand wraps after use by the boxers. Instead, after the hand wraps have been unwrapped from the hands in question, the wraps are generally stuffed loosely in a gym bag, pocket, or locker.

When stored in this manner, the planar surfaces of the wrap become folded, creased or wrinkled, making the wrap difficult if not impossible to reapply in the smooth manner preferred.

Even if the boxer were to take the trouble to roll the wrap about itself in an ad hoc manner, the resulting bundle is often generally creased and folded in numerous places and unrolls by the time it is to be reused, making it little better than if it were stored loosely to begin with.

Loose or balled-up wraps also have the undesirable tendency to become tangled with other clothing or equipment. When this happens, not only does the wrap become difficult to extract and reuse itself, but also the wrap interferes with the use of the other clothing or equipment. Needless to say, a boxer or other sports enthusiast faced with such entangled items is at least inconvenienced and frustrated, and may even wind up distracted and enraged before the boxing exercise ever begins, which is generally not desirable.

A wrap often has a loop attached to one of its ends for placing over the boxer's fingers or hands at the beginning of the wrapping operation. Conversely, hook-and-eye fasteners, such as so-called "VELCRO", are often supplied at the opposite end of the length of material, that is, the end which is destined to be at the exterior of the finished, wrapped hand. Such hook-and-eye fasteners assist in fixing the outer end of the cloth-like material to the user's hand so that it does not unwind. Such loops or hook-and-eye fasteners only exacerbate the aforementioned tendency for the wrap to become undesirably entangled during storage.

Furthermore, it is generally important for the boxer (or the trainer assisting such boxer) to be able to locate the looped end of the wrap so that the wrap can be started with the loop to the inside of the boxer's hand. Unfortunately, it may be difficult to find the looped end of a wrap stored loosely or balled up under current practices, especially when it is mixed in or hidden under other work-out items. Additional time may need to be spent searching for one's wrap or other equipment. Such time spent in preparing to work out, rather than in working out, is all the more undesirable because time is often at a premium in boxers' workouts, especially when training in one of today's over-subscribed boxing facilities.

The inconvenience of removal, storage, and reuse under current practices is only worse after the wrap has been used in a strenuous work-out and is damp with perspiration. Under such circumstances, the undesirable folds, wrinkles and creases of the wrap stored under current practices become even more rigidly set or stiffened as the perspiration dries. In such condition, it takes even longer to reapply the wrap, as increased efforts are required to untwist and uncrinkle the now stiff material, as it is being applied to the boxer's hand, such efforts are often not even successful in straightening out the wrap. The reapplication of the wrap in the smooth, planar manner preferred is thus rendered more difficult, if not impossible, as the twists, wrinkles or unevenness of each, stiff layer interfere with the smooth application of succeeding, overlying layers.

Furthermore, even if a previously used wrap is successfully applied, the odor of perspiration emanating from the finished wrap is sometimes not desirable.

There is thus a need for the wrap to be removed and stored in such a way that it can be reused conveniently and without excessive perspiration odor from such reuse.

There is further need for storing the cloth material used for hand wraps in a way that allows the wraps to be oriented and deployed from a stored position as quickly as possible, thereby maximizing the boxer's training, warm-up, or work-out time.

It would be of great benefit for boxers to be able to apply wraps to their hands by themselves, without needing the assistance of another person.

It would likewise be of great benefit to a boxer to have a means available for applying the wrap to one hand by using the other hand.

It is also desirable, whether the boxer applies the wrap him- or herself, or uses a second person, to be able to apply a wrap equally effectively with the left or with the right hand.

It is desirable for the boxer, without assistance, to be able to apply the appropriate amount of tensioning to the wrap to assure proper fit, and in a way that minimizes the amount of creasing or twisting of the wrap when it is applied.

SUMMARY OF THE INVENTION

An applicator for a wrap for a boxer's hand, in accordance with the present invention, has a spool with a spindle extending from one of the opposite ends of the spool. The surface of the spool is dimensioned to receive both of the side edges of the flexible, planar material which comprises the wrap, all without needing to fold or crease the wrap. There is deodorant associated with the applicator according to this aspect of the present invention.

In one preferred embodiment, the spool and the spindle are secured so as to be non-rotatable relative to each other under a predetermined amount of tangential force. In this way, the person holding the applicator can apply tension to the wrap while the wrap is being applied to the boxer's hand. The spool is friction fit relative to the spindle, so that when tangential force is applied to the spool above the predetermined amount, the spool rotates.

In another preferred embodiment of the present invention, the spool and the spindle are affixed to each other non-rotatably, so that tension is applied to the wrap whenever the spindle is pulled away from the hand being wrapped, and the spool will only rotate if the user manually rotates the associated spindle.

Yet another version of the present invention has one spindle extending from one end of the spool, and a second spindle extending from the opposite end of the spool. This arrangement means that there is always one spindle positioned away from the boxer's hand being wrapped, and such "distal" spindle is the one which is most convenient to be grabbed by the other hand to accomplish the desired wrap.

In still another aspect of the present invention, there are flanges at the opposite ends of the spool extending radially outwardly from the receiving surface of the spool. The size of the flanges is selected so that they extend a radial distance which will not be any greater than the radial thickness of a standard wrap received on the spool. A reclosable strap extends from the flanges across the receiving surface. By virtue of the radial size of the flanges, the strap, when closed, contacts the wrap to keep its end from unrolling.

Any of a variety of deodorants can be associated with the applicator of the present invention. One possibility is to make the receiving surface of the spool out of cedar wood. Alternately, the spool can have permeable walls defining a chamber, and deodorizing beads can be placed in the chamber.

BRIEF DESCRIPTION OF THE DRAWING

The invention will be better understood by reference to the following specification, for which a drawing is provided as described below. It is understood that the invention is not intended to be limited by the specification or drawing, and that the features of the invention are not necessarily shown to scale in such drawing. On the contrary, certain features of the invention are shown more prominently in the drawing to better illustrate the invention.

DETAILED DESCRIPTION

Figure 1:
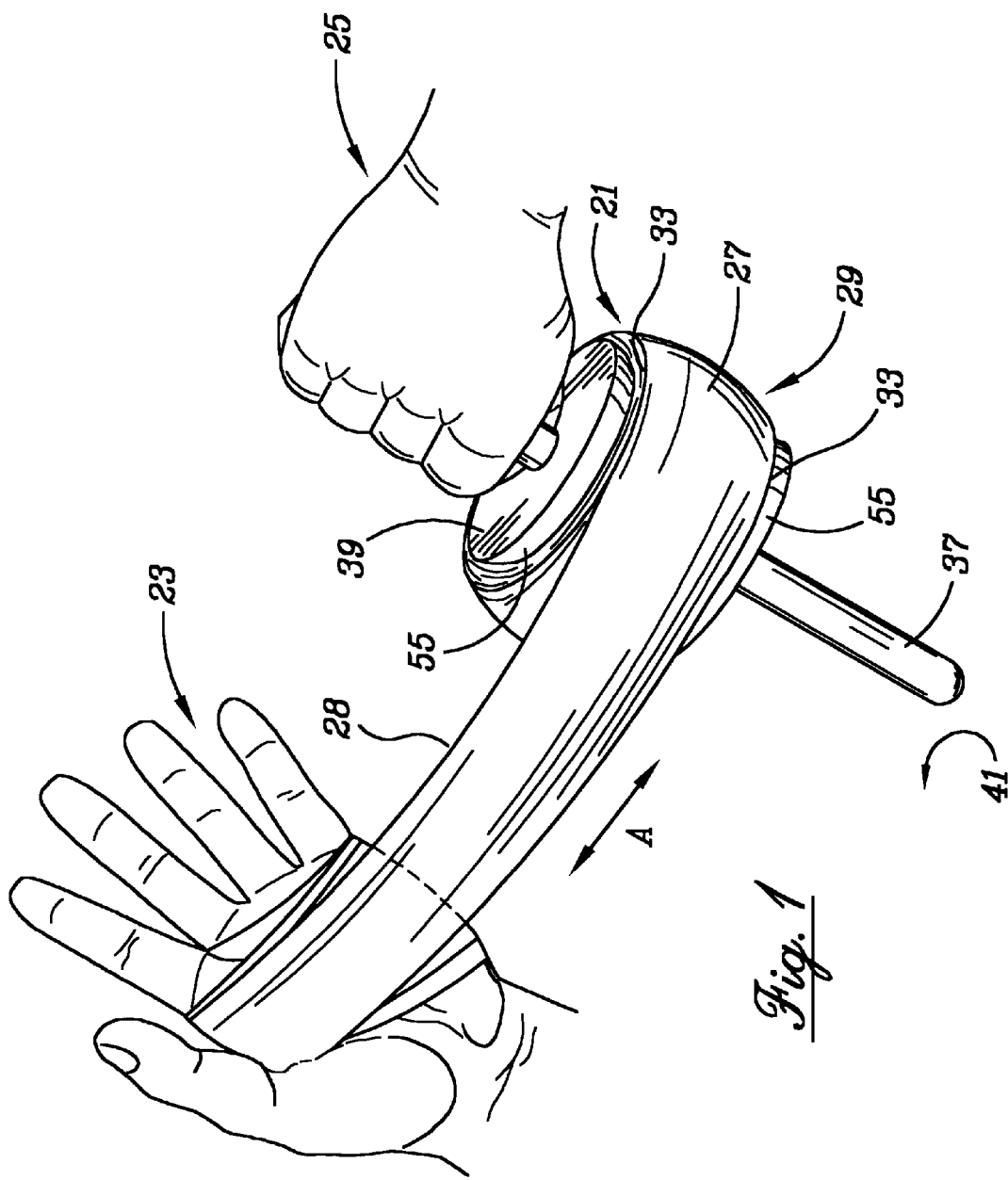
FIG. 1 is a perspective view of an applicator according the present invention being held by a boxer in one hand while applying a wrap to the other hand.

Referring now to the drawing, and in particular to FIGS. 1–4, a device or applicator 21, according to the present invention, is well-suited for correctly and optimally enwrapping one hand 23 of a boxer or other sports enthusiast with a web of flexible, ribbon-like wrap 27. The applicator 21 allows hand 23 to be wrapped merely by using the other hand 25, rather than the two hands generally required. Applicator 21 includes a spool 29 with a circumferential receiving surface which is long (or wide) enough to receive both side edges 33 of the wrap 27 thereon without needing to fold or crease the wrap 27. Wrap 27 is generally made out of cloth, but may be formed of other suitable, flexible tape material, such as polymeric material.

Figure 4:
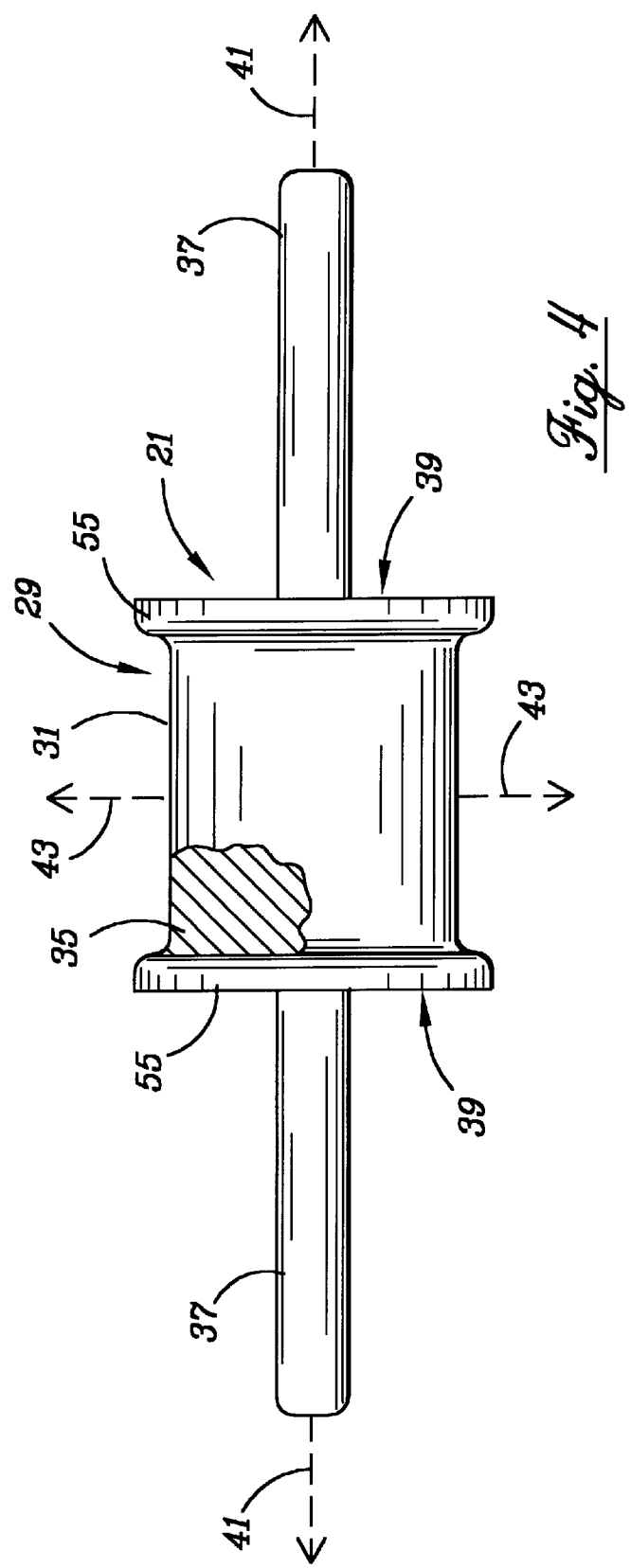
FIG. 4 is a side, elevational view of the invention without the wrap received thereon.

Spool 29 is equipped with means for deodorizing wrap 27 received thereon. In this embodiment, such deodorizing is accomplished by making receiving surface 31 out of cedar wood, or, alternately, making spool 29 from a piece of cedar wood which extends from the inside 35 of spool 29 radially outwardly to receiving surface 31 (FIG. 4).

In the illustrated embodiment, spool 29 is centrally and axially mounted between a pair of the spindles 37. Otherwise stated, one spindle 37 extends from one end 39 of spool 29, and the other spindle 37 extends outwardly in the opposite direction from the other, opposite end 39 of spool 29.

Applicator 21 is radially symmetric about central longitudinal axis 41. Furthermore, applicator 21 is also symmetric about a central, transverse axis 43. Such transverse symmetry has the advantage that, when either of the spool ends 39 is facing the boxer, there is a spindle 37 extending away from the boxer which can thus be grabbed by the boxer's free hand 25 to accomplish the desired wrapping of hand 23, as shown in FIG. 1. The boxer thus does not need to be as concerned with proper orientation of applicator 21 since either one of two opposite orientations is available. This increases the convenience of using applicator 21 and the speed with which hand 23 can be wrapped.

Spool 29 is preferably secured to spindle 37 so as to be non-rotatable about axis 41 relative to spindle 37. In this way, when the boxer's hand 23 and applicator 21 are moved relatively away from each other, portion 28 of wrap 27 between spool 29 and hand 23 experiences tensile forces in the direction of arrows A. As such, portion 28 becomes tensioned, and such tension is desirable for optimal application of wrap 27.

Alternately, spool 29 may be friction-fit onto spindle 37 so that a predetermined amount of tangential force (in the directions of arrows A (FIG. 1)) can be experienced by spool 29 without inducing rotation thereof. Tangential force in excess of such predetermined amount will cause spool 29 to rotate. As such, by selectively pulling hand 23 and applicator 21 apart from each other during the wrapping operation, not only is suitable tension applied during the wrapping process, but additional amounts of cloth wrap 27 may be dispensed from applicator 21 for placement on hand 23.

Figure 2:
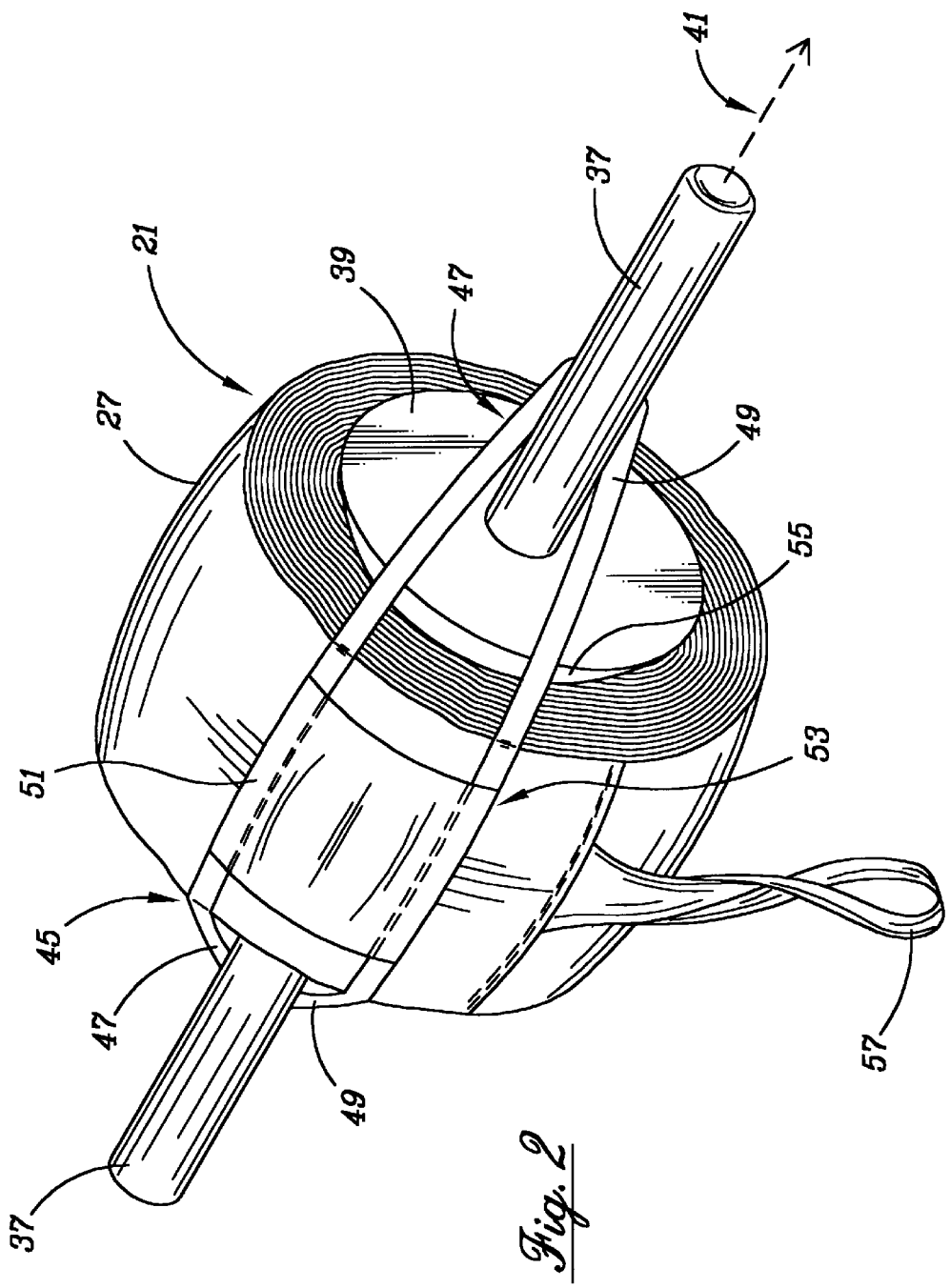
FIG. 2 is a perspective view of the applicator of FIG. 1 with the wrap fully received thereon.
Figure 3:
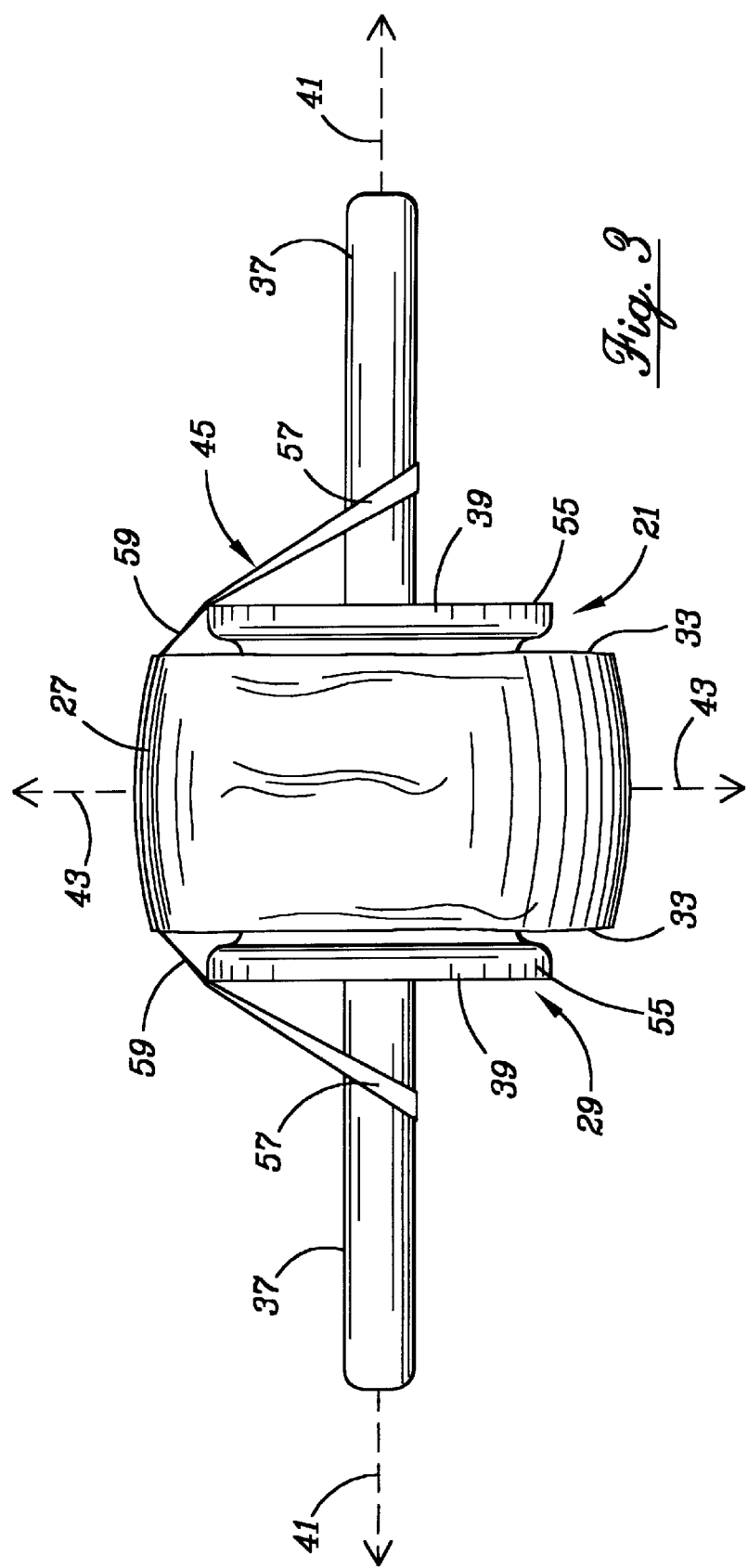
FIG. 3 is a side, elevational view of the applicator and wrap shown in FIG. 2.

Referring now more particularly to FIGS. 2 and 3, applicator 21 optionally includes a reclosable strap 45 for keeping wrap 27 in its fully rolled-up, stored position shown in FIGS. 2 and 3. Reclosable strap 45 has opposite ends 47 secured by any suitable means at or near spool ends 39. Strap 45 thus extends across receiving surface 31, and across the rolled wrap 27 received thereon so as to hold wrap 37 in place. In this embodiment, strap ends 47 comprise loops 49 which are releasably engaged around portions of the spindles 37. A medial portion 51 of strap 45 engages outer end 53 of wrap 27. Medial portion 51 exerts an inwardly directed, radial force against outer end 53 of wrap 27, either by means of elastic properties of strap 45 or as a result of radial compression of the rolled cloth wrap 27 received on receiving surface 31. The inwardly directed force from strap 45 helps to keep outer end 53 from unrolling.

As best seen in FIGS. 3 and 4, spool 29 is structured to include flanges 55 at opposite spool ends 39. Flanges 55 extend radially outwardly from receiving surface 31 by a radial distance not greater than the anticipated radial thickness of wrap 27 when fully received on receiving surface 31. As such, reclosable strap 45 is positioned so that strap portions 59 extend from respective outer edges of the flanges 55 across receiving surface 31, and, importantly, in substantial contact with outer end 53 of wrap 27. Flanges 55 thus provide strap 45 with a pair of "fulcrums" in this embodiment, which ultimately further assist in keeping outer end 53 of wrap 27 from unrolling from spool 29.

The use and operation of the present invention is readily appreciated from the foregoing description. Cloth wrap 27 is stored conveniently and optimally on applicator 21 in the configuration shown in FIG. 2. That is, both side edges 33 of wrap 27 are received on surface 31. This, in turn, allows the flexible planar surface of wrap 27 to be disposed in overlying, rolled layers without needing to fold or crease the planar surfaces of wrap 27. Strap 45 retains wrap 27 in its stored position shown in FIG. 2, and the wrap 27 can be transported with little fear of it unrolling by virtue of reclosable strap 45 secured against outer end 53 of wrap 27.

The end of the wrap (not shown) stored immediately adjacent receiving surface 31 is often equipped with hook-and-eye or Velcro fasteners. If so, then storing wrap 27 with the hook-and-eye fasteners secured to each other around receiving surface 31 further improves application of the wrap to the hand, as will be discussed below.

Applicator 21 is used to apply wrap 27 to hand 23 as follows. Strap 45 is released from its position across outer end 53. Outer end 53 of wrap 27 will generally include loop 57 in the accessible position shown in FIG. 2. If so, loop 57 is then readily placed over fingers or around the palm of hand 23 to begin the wrapping operation. Either of spindles 37 is grabbed by the other "free" hand 25, and the axis 41 of applicator 21 is oriented generally parallel to the extension of hand 23.

Planar surface of wrap 27 is then applied, substantially without creases or twists, to the knuckles and metacarpal region of hand 23, in successive, overlying layers. The length of cloth wrap 27 is unrolled from spool 29 and applied to hand 23 by orbiting applicator 21 and hand 23 relative to each other. One preferred way of holding applicator 21 relative to hand 23 is shown in FIG. 1. By grasping the spindle 37 which extends away from the boxer, the arms of the boxer do not "cross" during the orbiting of the applicator 21 and hand 23 relative to each other.

During the above-described orbiting, the fixed or friction-fit relationship between spool 29 and spindles 37 allows a suitable amount of tension to be maintained on the cloth wrap portion 28 extending between hand 23 and spool 21. This tensioning not only keeps wrap 27 from folding or creasing, but also maintains wrap 27 tightly secured around hand 23 for the upcoming work-out or other activity. The aforementioned tension is readily applied merely by pulling hand 23 and applicator 21 away from each other so that tensile force in the direction of arrows "A" is applied to portion 28 between receiving surface 31 of spool 29 and hand 23.

If needed during the foregoing operations, additional length of wrap 27 may be unrolled from applicator 21. Such unwinding is accomplished by rotating spindle 37 about axis 41 with the fingers of hand 25, in the case where spool 29 is non-rotatably affixed to spindles 37, or by applying an appropriate amount of tangential force to receiving surface 31, in the case where spool 29 and spindles 37 are friction-fit. In the preferred embodiment, the diameter of spool 29 is selected so that the "average" circumference of wrap 27 recieved thereon roughly corresponds to the average circumference of the hand being wrapped. Otherwise stated, on average, the length of wrap contained in a 360 degree arc on spool 29 is about equal to the circumference of an average boxer's hand. A complete, 360-degree orbit of the applicator 21 about the hand 23 thus unwinds a length of wrap 27 corresponding to the hand 23 being wrapped. As such, the need to rotate spool 29 about its axis 41 during the wrapping operation is minimized, thus further easing the wrapping operation described above.

Wrapping of hand 23 thus proceeds until wrap 27 has been substantially completely unwound from receiving surface 31 of spool 29. If, as mentioned above, the end of the wrap adjacent to the spool receiving surface 31 was secured to itself by hook-and-eye fasteners, then, even when wrap 27 has been substantially unwound, tension can be maintained on cloth wrap portion 28 without fear of wrap 27 suddenly separating from receiving surface 31, so long as the hook-and-eye fasteners have not been released. The wrap is thus completed by unfastening the hook-and-eye fasteners at the interior end of wrap 27 and resecuring such hook-and-eye fasteners to hand 23 in a well-known manner.

Applicator 21 is used to remove and store wrap 27 for reuse in a substantially reverse manner to the operations discussed above. Briefly, the hook-and-eye fasteners typically found at the outside of the wrap 27, when applied to the user's hand 23, are unfastened and looped around receiving surface 31. This end of wrap 27 will be at the inside of the rolled wrap 27 when it is fully received on applicator 21. The orbiting of spool 29 and hand 23 relative to each other is accomplished in a reverse fashion to that discussed previously, and spool 29 is suitably rotated about its longitudinal axis 41 to take up wrap 27 as required. The various features of the applicator 21 discussed above allow cloth wrap 27 to be received on receiving surface 31 in a planar (untwisted), wrinkle-free and untangled manner.

When wrap 27 has been fully received on applicator 21, reclosable strap 45 is re-extended across receiving surface 31 and outer end 53 to hold wrap 27 in a rolled, stored configuration. By providing spool 29 and, in particular, receiving surface 31, with deodorizing cedar wood, wrap 27 is deodorized whenever it is stored on spool 29. This has obvious advantages, especially if wrap 27 has been reused repeatedly or in a strenuous, perspiration-inducing workout.

It will be appreciated that various alternatives and modifications to the illustrated embodiment can be made, which are also within the scope of the present invention. For example, a single one of the spindles 37 can be supplied rather than the pair illustrated in FIGS. 1–4.

Figure 5:
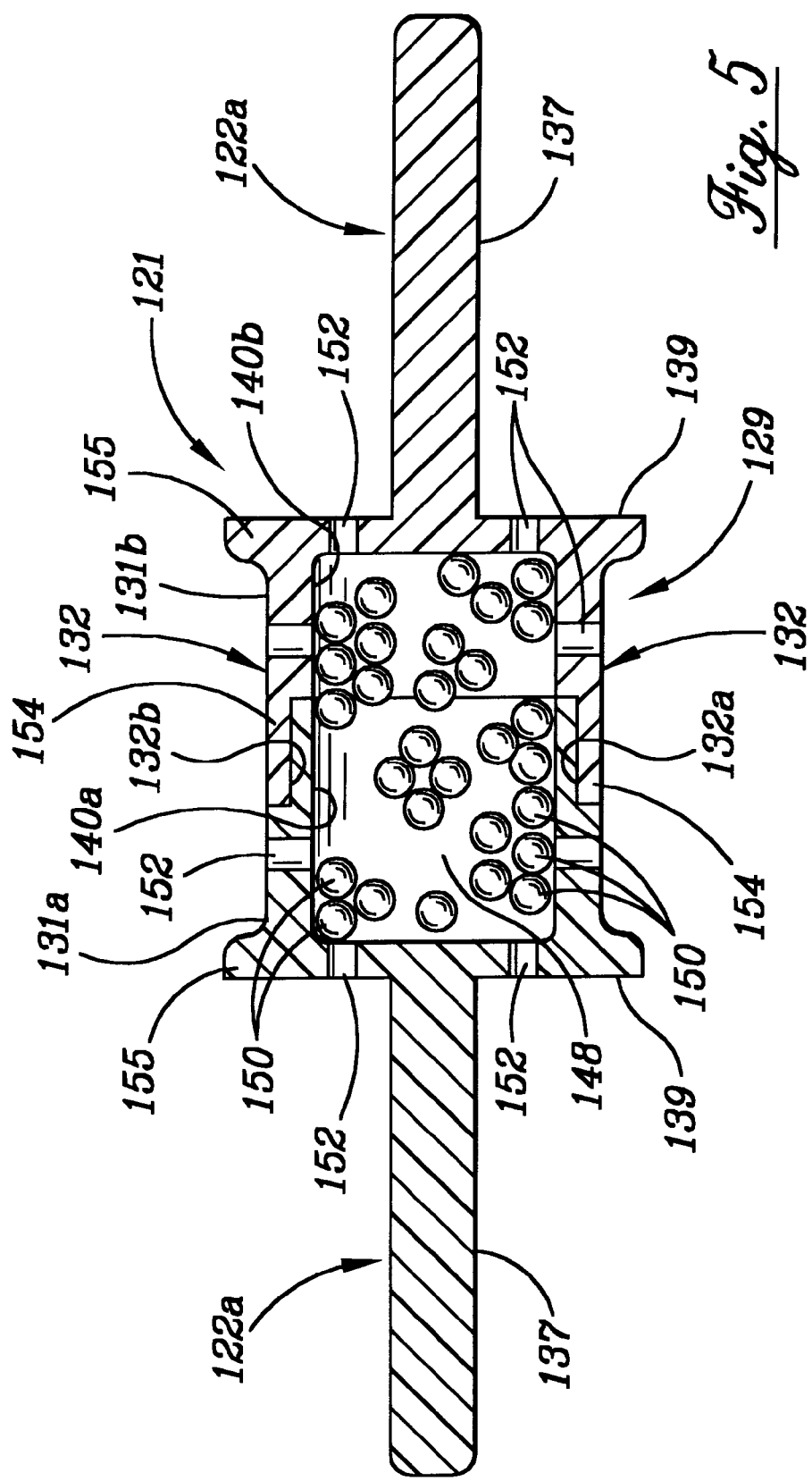
FIG. 5 is a cross-sectional view of an alternative embodiment of the present invention.

A further alternative embodiment is illustrated in FIG. 5. The applicator 121 of FIG. 5 is structurally similar to that illustrated in FIGS. 1–4, except that it is comprised of polymeric or plastic material formed as two mating halves 122a, 122b. Each of the halves 122a, 122b has a spindle 137 and flange 155 formed therein. Each of the halves 122a, 122b also has respective receiving surfaces 131a, 131b extending outwardly from respective flanges 155. The inner, opposing edges of receiving surfaces 131a, 131b have respective mating flanges 132a, 132b so that when the two halves 122a, 122b are assembled, the resulting, cylindrical receiving surface 132 has a length sufficient to receive cloth wrap 27 thereon without folding or creasing.

Significantly, applicator halves 122a, 122b have respective, inner walls 140a, 140b opposite receiving surfaces 131a, 131b. Inner walls 140a, 140b define a hollow chamber 148 within the resulting spool 129. Chamber 148 is filled with suitable deodorizing material. Preferably, such deodorizing material is applied to a suitable carrier, such as beads 150. The contact of such deodorized beads 150 with each other and inner walls 140a, 140b releases the deodorizing agents in a manner known in the art.

Importantly, a plurality of passages 152 extends between inner walls 140a, 140b and receiving surfaces 131a, 131b. As such, inner walls 140a, 140b, and receiving surfaces 131a, 131b define permeable cylindrical wall 154. Optionally, passages 152 can extend through spool ends 139 to render such ends permeable as well. It will be appreciated that permeable wall 154 and permeable end 139 permit the deodorant released from deodorizing beads 150 to escape from chamber 148 and deodorize wrap 27 (FIGS. 1 and 2) when received on receiving surfaces 131a, 131b.

In addition to the advantages apparent from the foregoing description, the present invention permits a hand wrap to be removed and stored without folds, creases or wrinkles, all of which are especially severe when the wrap dries and becomes stiff with perspiration.

Storing the wrap in a smooth, wrinkle-free manner makes it easier to reapply the wrap smoothly and in a wrinkle-free state.

The typically tangled mess of a used hand wrap stuffed in a gym bag is substantially eliminated. No longer does a boxer need to rifle through his or her equipment first to find the hand wrap, then to find the correct end of the hand wrap. Instead, the hand wrap is stored in a compact, yet easily identifiable form so it can be quickly taken out and applied prior to the workout, thus saving time and aggravation.

As a further advantage, the wrap is deodorized simply by storing the wrap according to the present invention.

As yet another advantage, the present invention allows appropriate tension to be applied to the wrap during its application, thereby assuring optimal fit around the boxer's hand.

As still another advantage, the wrap is both received on and deployed from the applicator quickly and conveniently. If the wrap has a looped end, such loop is stored to the outside of the rolled-up wrap and is thus ideally located to be put on the hand to be wrapped right at the outset, as required.

If the wrap has hook-and-eye fasteners at its opposite end, those hook-and-eye fasteners are advantageously securable adjacent the receiving surface of the spool. The hook-and-eye fasteners allow the wrap 27 to be kept in tension even when it is substantially unwound from spool 29.

The applicator according to the present invention has the further advantage of allowing boxers to apply wraps to hands without needing the assistance of another person. This, of course, saves time and, when such a second person is not readily available, it may save the boxer significant embarrassment or inconvenience.

As yet another advantage, whether the boxer applies the wrap him- or herself, or with the assistance of a second person, in either event, one-handed application is possible.

It is understood that the foregoing invention has been described with reference to certain preferred embodiments and alternatives thereto. Still further variations and alternatives can be readily contemplated by one skilled in the art, and such alternatives are within the scope of the present invention, as well as other alternatives which skill or fancy may suggest. Thus, the scope of the present invention is defined by the following claims and equivalents thereto.

What is claimed is:

1. An applicator for a wrap of a type used for a boxer's hand, the wrap being formed from flexible, planar material extending over a length and having a width extending to opposite side edges, the wrap dimensioned so that the wrap has an overall, ribbon-like form, the applicator comprising:

a spool having a circumferential receiving surface of sufficient axial length to receive both of the side edges of the wrap thereon without needing to fold or crease the wrap, the spool having a circumference substantially corresponding to the average circumference of the hand to be wrapped;

means for deodorizing the wrap provided in the spool; and at least one spindle secured to and extending outwardly from one of the opposite ends of the spool.

2. The applicator of claim 1, wherein the spool is secured to the spindle to remain non-rotatable relative to the spindle under a predetermined amount of tangential force applied to the spool, thereby permitting tension to be applied to the wrap while the wrap is being applied to the boxer's hand.

3. The applicator of claim 2, wherein the spool is friction fit relative to the spindle, the spool rotating when tangential force above the predetermined amount is applied to the spool.

4. The applicator of claim 1, wherein the spool is secured to be non-rotatable relative to the spindle.

5. The applicator of claim 1, further comprising means for operatively positioning the applicator in either one of two opposite orientations relative to the hand to be wrapped.

6. The applicator of claim 5, wherein the positioning means comprises a pair of the spindles, one spindle extending from one end of the spool, the second spindle extending from the opposite end of the spool, whereby, when either end of the spool is facing the boxer, one of the spindles extends away from the boxer and thus can be grabbed by the boxer's free hand to accomplish the desired wrapping.

7. The applicator of claim 1, further comprising means for keeping the outer end of the wrap from unrolling from the spool.

8. The applicator of claim 7, wherein the keeping means comprises a reclosable strap extending across the receiving surface of the spool.

9. The applicator of claim 1, further comprising flanges at the opposite ends of the spool, the flanges extending radially outward from the receiving surface.

10. The applicator of claim 9, wherein the flanges extend a radial distance not greater than the radial thickness of the wrap when fully received on the receiving surface.

11. The applicator of claim 10, further comprising a reclosable strap extending from the flanges across the receiving surface of the spool, whereby the strap, when closed, contacts the wrap when fully received thereon to keep the end of the wrap from unrolling.

12. The applicator of claim 1, wherein the deodorizing means comprises cedar wood.

13. The applicator of claim 12, wherein the cedar wood comprises at least a portion of the receiving surface.

14. The applicator of claim 13, wherein the spool comprises a solid piece of the cedar wood extending radially from inside the spool to the receiving surface.

15. The applicator of claim 13, wherein the spool comprises a solid piece of the cedar wood extending radially from inside the spool to the receiving surface.

16. The applicator of claim 1, further comprising a hollow chamber defined in the spool, and wherein the deodorizing means comprises a carrier in the chamber having deodorant associated therewith.

17. The applicator of claim 16, wherein the carrier comprises a plurality of beads.

18. The applicator of claim 16, wherein the spool comprises two pieces formed of polymeric material, the pieces being separable from each other to provide access to the chamber and the carrier therein.

19. An article for applying a wrap of the type used in sports to a first hand while holding the article in a second hand, the wrap being formed from flexible, planar material extending over a length and having a width extending to opposite side edges, the wrap dimensioned so that the wrap has an overall, ribbon-like form, the article comprising:

a spool having a circumferential receiving surface on which the wrap is removably wound, the receiving surface having an axial length substantially corresponding to the width of the wrap to receive both of the side edges of the wrap on the receiving surface without needing to fold or crease the planar material of the wrap, the spool having a circumference substantially corresponding to the average circumference of the hand to be wrapped; and a spindle secured to and extending outwardly from the spool, the spindle being non-rotatable relative to the spool, the second hand grasping the spindle while the wrap is being applied to the first hand, the wrap having a tensioned portion between the spool and the first hand to which the wrap is being applied when the spool is moved away from the first hand without rotation of the spool.

20. The article of claim 19, further comprising:

means provided in the spool for deodorizing the wrap; and means for keeping the outside end of the wrap from unrolling from the spool.

21. The article of claim 20, wherein the deodorizing means comprises cedar wood on the receiving surface of the spool, and wherein the keeping means comprises a reclosable strap extending across the receiving surface.

22. The article of claim 20, further comprising a hollow chamber defined in the spool, wherein the deodorizing means comprises a plurality of beads having deodorant associated therewith and received in the chamber, and wherein the spool comprises two pieces formed of polymeric material, the pieces being separable from each other to provide access to the chamber and the beads therein.

* * * * *